(12) United States Patent
Borovik et al.

(10) Patent No.: US 7,084,080 B2
(45) Date of Patent: Aug. 1, 2006

(54) SILICON SOURCE REAGENT COMPOSITIONS, AND METHOD OF MAKING AND USING SAME FOR MICROELECTRONIC DEVICE STRUCTURE

(75) Inventors: Alexander S. Borovik, Hartford, CT (US); Ziyun Wang, New Milford, CT (US); Chongying Xu, New Milford, CT (US); Thomas H. Baum, New Fairfield, CT (US); Brian L. Benac, Austin, TX (US)

(73) Assignee: Advanced Technology Materials, Inc., Danbury, CT (US)

(*) Notice: Subject to any disclaimer, the term of this patent is extended or adjusted under 35 U.S.C. 154(b) by 0 days.

(21) Appl. No.: 10/112,517

(22) Filed: Mar. 29, 2002

(65) Prior Publication Data

US 2002/0180028 A1    Dec. 5, 2002

Related U.S. Application Data

(63) Continuation-in-part of application No. 09/954,831, filed on Sep. 18, 2001, now Pat. No. 6,869,638, which is a continuation-in-part of application No. 09/823,196, filed on Mar. 30, 2001.

(51) Int. Cl.
   *H01L 21/31*    (2006.01)
   *H01L 21/469*   (2006.01)
   *C07F 7/04*     (2006.01)
   *C07F 7/10*     (2006.01)
   *C07F 7/08*     (2006.01)

(52) U.S. Cl. .............. 438/794; 438/790; 556/413; 556/466

(58) Field of Classification Search ............ 556/410, 556/412, 413, 466; 438/789, 790, 793, 794, 438/787, 788, 785
See application file for complete search history.

(56) References Cited

U.S. PATENT DOCUMENTS

| | | | |
|---|---|---|---|
| 3,467,686 A * | 9/1969 | Creamer ............... | 556/410 |
| 4,491,669 A | 1/1985 | Arkles et al. | |
| 4,499,198 A * | 2/1985 | Pullukat et al. ........ | 502/104 |
| 4,895,709 A | 1/1990 | Laine | |
| 5,003,092 A | 3/1991 | Beachley, Jr. | |
| 5,008,422 A * | 4/1991 | Blum et al. ........... | 556/412 |
| 5,084,588 A * | 1/1992 | Ocheltree et al. ...... | 556/466 |
| 5,139,825 A | 8/1992 | Gordon et al. | |
| 5,178,911 A | 1/1993 | Gordon et al. | |
| 5,204,314 A | 4/1993 | Kirlin et al. | |
| 5,210,254 A * | 5/1993 | Ritscher et al. ........ | 556/466 |
| 5,225,561 A | 7/1993 | Kirlin et al. | |
| 5,252,518 A | 10/1993 | Sandhu et al. | |
| 5,268,496 A | 12/1993 | Geisberger | |
| 5,280,012 A | 1/1994 | Kirlin et al. | |
| 5,362,328 A | 11/1994 | Gardiner et al. | |
| 5,417,823 A | 5/1995 | Narula et al. | |
| 5,453,494 A | 9/1995 | Kirlin et al. | |
| 5,536,323 A | 7/1996 | Kirlin et al. | |
| 5,583,205 A | 12/1996 | Rees, Jr. | |
| 5,616,755 A * | 4/1997 | Seiler et al. .......... | 556/413 |
| 5,698,726 A * | 12/1997 | Rauleder et al. ....... | 556/413 |
| 5,726,294 A | 3/1998 | Rees, Jr. | |
| 5,820,664 A | 10/1998 | Gardiner et al. | |
| 5,820,678 A | 10/1998 | Hubert et al. | |
| 5,876,503 A | 3/1999 | Roeder et al. | |
| 5,919,522 A | 7/1999 | Baum et al. | |
| 5,924,012 A | 7/1999 | Vaartstra | |
| 5,972,430 A | 10/1999 | DiMeo, Jr. | |
| 5,976,991 A | 11/1999 | Laxman et al. | |
| 6,013,553 A | 1/2000 | Wallace et al. | |
| 6,015,917 A | 1/2000 | Bhandari et al. | |
| 6,020,243 A | 2/2000 | Wallace et al. | |
| 6,060,406 A | 5/2000 | Alers et al. | |
| 6,110,529 A | 8/2000 | Gardiner et al. | |
| 6,159,855 A | 12/2000 | Vaartstra | |
| 6,177,135 B1 | 1/2001 | Hintermaier et al. | |
| 6,348,412 B1 | 2/2002 | Vaartstra | |

FOREIGN PATENT DOCUMENTS

| | | |
|---|---|---|
| JP | 06-293778 A | 10/1994 |
| WO | WO/00/67300 | 11/2000 |

OTHER PUBLICATIONS

U.S. Appl. No. 09/414,133, filed Oct. 7, 1999, Thomas H. Baum et al.
U.S. Appl. No. 07/927,134, filed Aug. 7, 1992, Peter S. Kirlin et al.
U.S. Appl. No. 07/615,303, filed Nov. 19, 1990, Duncan W. Brown.
U.S. Appl. No. 07/549,389, filed Jul. 6, 1990, Peter S. Kirline, et al.
R. Gordon, D. Hoffman and U. Riaz report (Chem. Mater. 1990, 2, 480-482).
Jones, et al., "MOCVD of Zirconia Thin Films by Direct Liquid Injection Using a New Class of Zirconium Precursor", Chem. Vap. Dep., vol. 4, 1998, pp. 46-49.
D.C. Bradley, et al., "Metalorganic Compounds Containing Metal-Nitrogen Bonds: Part I, Some Dialkyamino Derivatives of Titanium and Zirconium", J. Chem. Soc., 1960, 3857).
D.C. Bradley, et al., "Metalorganic Compounds Containing Metal-Nitrogen Bonds: Part III. Dialkylamino Compounds of Tantalum", Canadian J. Chem., 40, 1355 (1962).

(Continued)

*Primary Examiner*—George Eckert
*Assistant Examiner*—Colleen E. Rodgers
(74) *Attorney, Agent, or Firm*—Maggie Chappuis; Tristan A. Fuierer; John Boyd

(57) ABSTRACT

A method of synthesizing an aminosilane source reagent composition, by reacting an aminosilane precursor compound with an amine source reagent compound in a solvent medium comprising at least one activating solvent component, to yield an aminosilane source reagent composition having less than 1000 ppm halogen.

26 Claims, 5 Drawing Sheets

OTHER PUBLICATIONS

S. Giles, et al., "Deposition of (Ti,Al)N thin films by organometallic chemical vapor deposition: thermodynamic predictions and experimental results", Elsevier Science, SA, Surface and Coatings Technology, 94-95 (1997), pp. 285-290.

Kozoh Sugiyama, et al., "Low Temperature Deposition of Metal Nitrides by Thermal Decomposition of Organometallic Compounds", Journal of the Electrochemical Society, vol. 122, No. 11, Nov. 1975.

R. Juza, et al., "Ammonothermal Synthesis of Magnesium and Beryilium Amides", Angew. Chem. Inte. Ed., 5, (2), 247 (1966).

Toshiro Maruyama, et al., "Silicon dioxide thin films prepared by chemical vapor deposition from tetrakis(diethylamino)silane and ozone", Applied Phys. Lett. 64, (21), May 23, 1994.

Toshiro Maruyama "Electrical Characterization of Silicon Dioxide Thin Films Prepared by Chemical Vapor Deposition from Tetrakis(diethylamino)silane and Ozone", Jpn. J. Appl. Phys. vol. 36 (1997) pp. L922-925, Part 2, No. 7B, Jul. 15, 1997.

Chi Ming Yam, et al., "Simple Acid-Based Hydrolytic Chemistry Approach to Molecular Self-Assembly: Thin Films of Long Chain Alcohols Terminated with Alkyl, Phenyl, and Acetylene Groups on Inorganic Oxides Surfaces", Langmuir, (1998), vol. 14, No. 24, pp. 6941-6947.

Wolfram Uhlig, "Darstellung neuartiger monomerer, oligomerer und polymerer Silyltriflate", Chem. Ber. 1992, 125, 47-53.

Yanjian Wan, et al., "Hydride and Fluoride Transfer Reactions Accompanying Nucleophilic Substitution at Pentacoordinate Silicon", J. Am. Chem. Soc. 1995, 117, 141-156.

Herbert H. Anderson, "Dialkylaminogermanes and dialkylaminosilanes", Harvard Univ. J. Am. Chem. Soc. (1952), 74, 1421-3.

* cited by examiner

SILICON SOURCE REAGENT COMPOSITIONS, AND METHOD OF MAKING AND USING SAME FOR MICROELECTRONIC DEVICE STRUCTURE

This patent application is a continuation in part of U.S. patent application Ser. No. 09/954,831 filed with the United States Patent and Trademark Office on Sep. 18, 2001 now U.S. Pat. No. 6,869,638 in the names of Thomas H. Baum, Chongying Xu, Bryan C. Hendrix and Jeffrey F. Roeder, which is a continuation in part of U.S. patent application Ser. No. 09/823,196 filed with the United States Patent and Trademark Office on Mar. 30, 2001 in the same names.

FIELD OF THE INVENTION

The present invention relates to silicon precursor compositions and their synthesis, and to the use of such silicon precursor compositions for the fabrication of microelectronic device structures, e.g., in the formation of gate dielectrics and silicon nitride barrier layers, in the manufacture of semiconductor integrated circuits, or in otherwise forming silicon-containing films on a substrate by chemical vapor deposition (CVD) utilizing such precursor compositions.

BACKGROUND OF THE INVENTION

The process of fabricating semiconductor integrated circuits generally includes the formation of such components as, gate oxides, high k dielectrics, low k dielectrics, barrier layers, etch stop layers and gate spacers. Such components often include silicon or silicon oxide in their compositions. For example, conventional gate dielectric materials may be formed from silicon dioxide, silicon oxy-nitride, silicon nitride or metal silicates.

Semiconductor devices such as field effect transistors (FET) and metal oxide semiconductor capacitors (MOS-caps), which are common in the electronics industry, include many of the components identified above. Such devices may be formed with dimensions that enable thousands or even millions of devices to be formed on a single-crystal substrate and interconnected to perform useful functions in an integrated circuit such as a microprocessor.

The general structure and operation of a field effect transistor is as follows. With reference to FIG. 1, a simplified field effect transistor is shown in cross-section. In a field effect transistor a portion of the substrate (or epi-layer) 100 near the surface is designated as the channel 120 during processing. Channel 120 is electrically connected to source 140 and drain 160, such that when a voltage difference exists between source 140 and drain 160, current will tend to flow through channel 120. The semiconducting characteristics of channel 120 are altered such that its resistivity may be controlled by the voltage applied to gate 200, a conductive layer overlying channel 120. Thus by changing the voltage on gate 200, more or less current can be made to flow through channel 120. Gate 200 and channel 120 are separated by gate dielectric 180; the gate dielectric is insulating, such that between gate 200 and channel 120 the current flow during operation is small compared to the source to drain current (although "tunneling" current is observed with thin dielectrics.) However, the gate dielectric allows the gate voltage to induce an electric field in channel 120, giving rise to the name "field effect transistor." The general structure of a MOS-cap can be visualized as layers 200, 180 and 120 of FIG. 1 without the source and drain. The MOS-cap functions as a capacitor.

$SiO_2$ represents the highest quality gate dielectric material 180 so far developed in silicon technology with low defects and low surface state density. One important advantage of $SiO_2$ is that it may be grown from the silicon substrate at elevated temperatures in an oxidizing environment. It is well known in the art, that thermally grown oxides tend to have fewer defects, (i.e. pinholes), than deposited materials. Thus, $SiO_2$ has persisted as the dielectric material in most silicon device structures.

Generally, integrated circuit performance and density may be enhanced by decreasing the size of the individual semiconductor devices on a chip. Unfortunately, field effect semiconductor devices produce an output signal that is proportional to the length of the channel, such that scaling reduces their output. This effect has generally been compensated for by decreasing the thickness of gate dielectric 180, thus bringing the gate in closer proximity to the channel and enhancing the field effect.

As devices have scaled to smaller and smaller dimensions, the gate dielectric thickness has continued to shrink. Although further scaling of devices is still possible, scaling of the gate dielectric thickness has almost reached its practical limit with the conventional gate dielectric materials: silicon dioxide, silicon oxy-nitride and silicon nitride. Further scaling of silicon dioxide gate dielectric thickness will involve problems such as: extremely thin layers allowing for large leakage currents due to direct tunneling through the oxide. Because such layers are formed literally from a few atomic layers, exact process control is required to repeatably produce such layers. Uniformity of coverage is also critical because device parameters may change dramatically based on the presence or absence of even a single monolayer of dielectric material. Finally, such thin layers form poor diffusion barriers to impurities and dopants.

Consequently, there is a need in the art for alternative dielectric materials, which can be formed in a thicker layer than silicon dioxide and yet still produce the same field effect performance. This performance is often expressed as "equivalent oxide thickness" (EOT). Although the alternative material layer may be thick, it has the equivalent effect of a much thinner layer of silicon dioxide (commonly called simply "oxide"). In order to have a physically thick layer with a low EOT, the dielectric constant of the insulating material must be increased. Many, if not most, of the attractive alternatives for achieving low equivalent oxide thicknesses are metal oxides, such as tantalum pentoxide, titanium dioxide, barium strontium titanate and other suitable thin films.

However, the formation of such metal oxides as gate dielectrics has been found to be problematic. At typical metal oxide deposition temperatures, the oxygen co-reactant or oxygen-containing precursor tends to oxidize the silicon substrate, producing a lower dielectric constant oxide layer at the interface between the substrate and the higher dielectric constant, gate dielectric material. It could be that the transition metal oxide acts as a catalytic source of activated oxygen, that the precursor molecules increase the oxygen activity or that oxygen from the precursor is incorporated in the growing oxide film. Whatever the cause, the presence of this interfacial oxide layer increases the effective oxide thickness, reducing the effectiveness of the alternative gate dielectric material. The existence of the interfacial oxide layer places a severe constraint on the performance of an alternative dielectric field effect device and therefore, is unacceptable.

The use of metal oxide and metal oxy-nitride thin films comprising Zr, Hf, Y, La, Lanthanide series elements, Ta, Ti and/or Al and silicates of these metal oxides and metal oxy-nitrides are regarded as potential material replacements of the $SiO_2$ gate oxides, (i.e., U.S. Pat. Nos. 6,159,855 and 6,013,553). However, to ensure a high integrity interface between the silicon and the gate dielectric film these films must be deposited at relatively low temperatures.

The source reagents and methodology employed to form such gate dielectric thin films are extremely critical for the provision of a gate structure having satisfactory electrical performance characteristics in the product device. Specifically, the source reagents and methodology must permit the gate dielectric thin film to form on a clean silicon surface, without the occurrence of side reactions producing predominantly silicon dioxide ($SiO_2$), locally doped $SiO_2$ and/or other impurities, that lower the dielectric constant and compromise the performance of the product microelectronic device. Accordingly, the absence of impurities is highly desirable.

Chemical vapor deposition (CVD) is the thin film deposition method of choice for high-density, large-scale fabrication of microelectronic device structures, and the semiconductor manufacturing industry has extensive expertise in its use. Metalorganic CVD (MOCVD) and more particularly atomic layer CVD (ALCVD) are particularly advantageous processes because they allow for lower deposition temperatures and stricter control of the stoichiometry and thickness of the formed layer.

In the formation of gate dielectrics and other semiconductor manufacturing applications it is essential to control the composition of the deposited thin film. The molar ratio(s) of the different elements in the thin film typically corresponds very closely to a predetermined value. Therefore, it is very important to select a precursor delivery system that allows for strict control of the precursors delivered into the CVD chamber. Precursor delivery systems are well known in the art of CVD, (i.e., U.S. Pat. No. 5,820,678, entitled "Solid Source MOCVD System" describes the bubbler delivery approach and U.S. Pat. No. 5,204,314, entitled "Method for Delivering an Involatile Reagent in Vapor Form to a CVD Reactor," and U.S. Pat. No. 5,536,323, entitled "Apparatus for Flash Vaporization Delivery of Reagents," describe the liquid delivery, flash vaporization approach).

Chemical vapor deposition (CVD) of silicon-containing films provides uniform coverage. Liquid CVD precursors enable direct delivery or liquid injection of the precursors into a CVD vaporizer unit. The accurate and precise delivery rate can be obtained through volumetric metering to achieve reproducible CVD metallization during VLSI device manufacturing.

Impurities that are known to lower the dielectric constant and/or increase leakage include among others, carbon and halides. Carbon and/or halide incorporation into the dielectric thin film would degrade leakage, dielectric constant, and overall electrical performance of the thin film. In contrast, nitrogen incorporation may exhibit some beneficial properties on the dielectric thin film.

Excess halide may adversely affect a gate dieletric thin film in either of two ways. Halide incorporation into a gate dielectric thin film, may directly affect the electronic nature of the film, thereby reducing device lifetime. Secondly, halide, such as chloride, leads to formation of hydrogen chloride during the decomposition of the precursor, which potentially affects the CVD chamber making the treatment of the effluent from the chamber more challenging.

Zr, Hf, Y, La, Lanthanide series elements, Ta, Ti, Al and/or silicon source reagents, specifically Zr and Hf-containing silicates such as $Zr_xSi_{1-x}O_2$, and $Hf_xSi_{1-x}O_2$ are of great interest for use as next generation gate dielectrics. These materials possess dielectric constant (k) values in the range of 10 to 20, depending on x, and allow the use of a physical thickness to prevent leakage by electron tunneling. Given the feature sizes of the VLSI devices, CVD is becoming a unique technique for depositing these materials.

In such applications, the choice of the zirconium or hafnium CVD source reagents and a compatible silicon source reagent is of critical importance for the successful deposition of high quality Zr or Hf silicate gate dielectric. Low temperature CVD silicon precursors are required to minimize the formation of interfacial silicon dioxide. Ideally, the precursors are compatible in solution and in vapor phase and decompose below 600° C. on substrate surfaces, forming Hf or Zr silicates in high purity and high density with no interfacial layer.

The source reagents must be thermally stable to avoid premature decomposition of such source reagents before they reach the CVD reaction chamber during the CVD process. Premature decomposition of source reagents not only results in undesirable accumulation of side products that will clog fluid flow conduits of the CVD apparatus, but also causes undesirable variations in composition of the deposited gate dielectric thin film. Further, particle formation can result in deleterious yields in device fabrication.

Further, Zr, Hf, Y, La, Lanthanide series elements, Ta, Ti, Al and/or silicon source reagents have to be chemically compatible with other source reagents used in the CVD process. "Chemically compatible" means that the source reagents will not undergo, undesirable side reactions with other co-deposited source reagents, and/or deleterious ligand exchange reactions that may alter the precursor properties, such as transport behavior, incorporation rates and film stoichiometries. Finally, Zr, Hf, Y, La, Lanthanide series elements, Ta, Ti, Al and/or silicon source reagents selected for MOCVD of dielectric thin films must be able to maintain their chemical identity over time when dissolved or suspended in organic solvents or used in conventional bubblers. Any change in chemical identity of source reagents in the solvent medium is deleterious since it impairs the ability of the CVD process to achieve repeatable delivery and film growth.

There is a continuing need in the art to provide improved Zr, Hf, Y, La, Lanthanide series elements, Ta, Ti, Al and/or silicon source reagents suitable for high efficiency CVD processes, for fabricating corresponding high quality gate dielectric, thin films.

Silicon amide source reagents are of great interest for use as low temperature CVD precursors in many applications, e.g., CVD of silicon nitride and early transition metal silicates. However, many commercially available silicon amides have unacceptably high levels of chloride.

Currently available synthetic routes result in poor yields and/or impure material. For example, Gerard Kannengiesser and Francois Damm, (*Bull. Soc. Chim. Fr.* (1967), (7), 2492–5) disclose the method outlined by equation (1) below and report a product yield of only about 20%.

$$SiCl_4 + 4R_2NMgBr \rightarrow Si(NR_2)_4 + 4MgBrCl \qquad (1)$$

R. Gordon, D. Hoffman and U. Riaz report (*Chem. Mater.* 1990, 2, 480–482) the synthesis of $Si(NMe_2)_4$ using $LiNMe_2$ and $SiCl_4$ in toluene in 60% yield. When, the same experiment was repeated by the inventors of the instant invention, the product contained chlorine content too high (a few percent) for semiconductor grade materials.

Therefore, it is one object of this invention to provide CVD precursors and CVD processes to deposit high dielectric constant thin films, having minimum carbon and halide incorporation and when deposited on a silicon substrate, minimal SiO$_2$ interlayer.

It is a further object of this invention to synthesize aminosilane source reagents in high yield and high purity.

It is a still further object of the present invention to provide CVD precursors and a CVD process to deposit silicon containing thin films, having minimum carbon and halide incorporation and when deposited on a silicon substrate, minimal SiO$_2$ interlayer.

It is another object of the invention to provide methods of forming silicon-containing films in the manufacturing of integrated circuits and other microelectronic device structures.

It is another object of the invention to provide a method of forming silicon-containing thin films on a substrate by metalorganic chemical vapor deposition (CVD) utilizing such novel silicon precursors and solution compositions.

The present invention relates to novel precursor compositions for low temperature (<600° C.) chemical vapor deposition (CVD) formation of silicon-containing films, and to associated methods of making and using such types of compositions.

Other objects and advantages of the present invention will be more fully apparent from the ensuing disclosure and appended claims.

SUMMARY OF THE INVENTION

The present invention relates to aminosilane source reagent compositions, and to a method of making, and using the same.

In one broad aspect, the present invention relates to silicon precursors having reduced oxygen and halogen content (relative to various corresponding commercial silicon source reagents) with utility for chemical vapor deposition (CVD) of silicon containing thin films of varying types, including silicon nitride, silicates, and doped silicate films (when a dopant co-precursor is utilized), as well as to a method for making and using such silicon precursors. More specifically, the silicon precursors of the present invention comprise a composition selected from the group consisting of:

  (2)

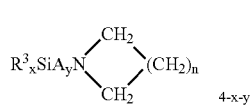  (3)

wherein R$^3$ is selected from the group consisting of hydrogen, C$_1$–C$_4$ alkyl, and C$_1$–C$_4$ alkoxy; x is from 0 to 3; Si is silicon; A is halogen; y is from 0 to 3; N is nitrogen; each of R$^1$ and R$^2$ is same or different and is independently selected from the group consisting of H, aryl, perfluoroaryl, C$_1$–C$_8$ alkyl, and C$_1$–C$_8$ perfluoroalkyl; and n is from 1–6.

In a further aspect, the present invention relates to novel, stable aminosilane source reagent compositions for chemical vapor deposition (CVD) of silicon-containing thin films as well as to methods of making and using same. More specifically, the present invention relates to novel aminosilane source reagent compositions having the formula,

  (2)

wherein R$^3$ is selected from the group consisting of hydrogen, C$_1$–C$_4$ alkyl, and C$_1$–C$_4$ alkoxy; x is from 0 to 3; Si is silicon; A is halogen; y is from 0 to 3; N is nitrogen; R$^1$ is methyl and R$^2$ ethyl.

In a further aspect, the present invention relates to a method of synthesizing an aminosilane source reagent composition, by reacting a silicon halide source reagent compound with an amine source reagent compound in a polar, activating solvent, to yield an aminosilane precursor having reduced halide content as compared to the existing commercial precursors.

In a specific aspect, the present invention provides a CVD process that uses the aforementioned aminosilane precursors, that may alternatively be in the form of a neat liquid, as well as solution compositions of solid and liquid precursors of such type, for deposition of silicon containing films (e.g., by direct liquid injection and vaporization). Vaporization may be effected by heating, acoustics, ultrasound or nebulization.

A still further aspect of the invention relates to a microelectronic device structure comprising a substrate having a chemical vapor deposited silicon-containing thin film layer on the substrate, wherein the silicon containing layer has been formed using a liquid-phase silicon precursor that is thermally stable at liquid delivery temperatures (at which the precursor liquid is vaporized to form a corresponding precursor vapor), but which is readily decomposable at chemical vapor deposition condition temperatures, to yield a silicon-containing film on the substrate with which the precursor vapor is contacted Other aspects, features, and embodiments of the invention will be more fully apparent from the ensuing disclosure and appended claims.

DETAILED DESCRIPTION OF THE INVENTION AND PREFERRED EMBODIEMENTS THEREOF

Figure 1:
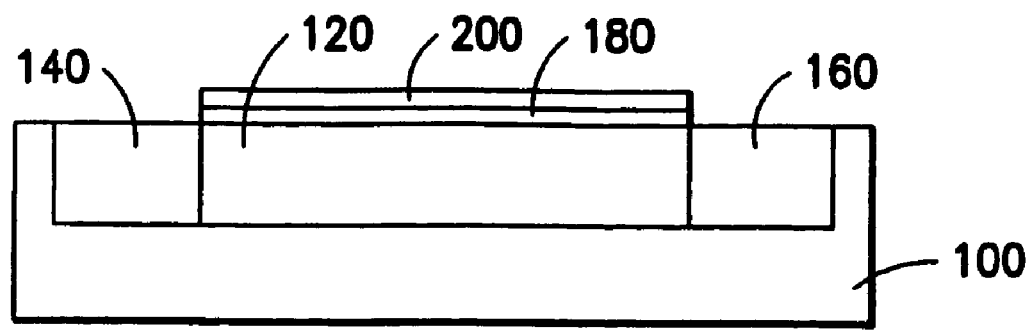
FIG. 1 is a cross-sectional view of a typical prior art integrated circuit field effect transistor.

The disclosure of the following United States patents and patent applications are hereby incorporated by reference in their respective entireties:

U.S. patent application Ser. No. 09/414,133 filed Oct. 7, 1999 in the names of Thomas H. Baum, et al.;

U.S. patent application Ser. No. 09/012,679 filed Jan. 23, 1998 in the names of Gautam Bhandari, et al., and issued Jan. 18, 2000 as U.S. Pat. No. 6,015,917;

U.S. patent application Ser. No. 08/979,465 filed Nov. 26, 1997 in the names of Frank DiMeo, Jr., et al., and issued Oct. 26, 1999 as U.S. Pat. No. 5,972,430;

U.S. patent application Ser. No. 08/835,768 filed Apr. 8, 1997 in the names of Thomas H. Baum, et al., and issued Jul. 6, 1999 as U.S. Pat. No. 5,919,522;

U.S. patent application Ser. No. 08/484,654 filed Jun. 7, 1995 in the names of Robin A. Gardiner et al., and issued Aug. 29, 2000 as U.S. Pat. No. 6,110,529;

U.S. patent application Ser. No. 08/414,504 filed Mar. 31, 1995 in the names of Robin A. Gardiner et al., and issued Oct. 13, 1998 as U.S. Pat. No. 5,820,664;

U.S. patent application Ser. No. 08/280,143 filed Jul. 25, 1994 in the names of Peter S. Kirlin, et al., and issued Jul. 16, 1996 as U.S. Pat. No. 5,536,323;

U.S. patent application Ser. No. 07/927,134, filed Aug. 7, 1992 in the same names;

U.S. patent application Ser. No. 07/807,807 filed Dec. 13, 1991 in the names of Peter S. Kirlin, et al., and issued Apr. 20, 1993 as U.S. Pat. No. 5,204,314;

U.S. patent application Ser. No. 08/181,800 filed Jan. 15, 1994 in the names of Peter S. Kirlin, et al., and issued Sep. 26, 1995 as U.S. Pat. No. 5,453,494;

U.S. patent application Ser. No. 07/918,141 filed Jul. 22, 1992 in the names of Peter S. Kirlin, et al., and issued Jan. 18, 1994 as U.S. Pat. No. 5,280,012;

U.S. application Ser. No. 07/615,303 filed Nov. 19, 1990;

U.S. patent application Ser. No. 07/581,631 filed Sep. 12, 1990 in the names of Peter S. Kirlin, et al., and issued Jul. 6, 1993 as U.S. Pat. No. 5,225,561.

U.S. patent application Ser. No. 07/549,389 filed Jul. 6, 1990 in the names of Peter S. Kirlin, et al.

U.S. patent application Ser. No. 08/758,599 filed Nov. 27, 1996 in the names of Jeffrey F. Roeder, et al., and issued Mar. 2, 1999 as U.S. Pat. No. 5,876,503.

The above-identified applications and patents variously describe source reagent compositions, their synthesis and formulation, as well as CVD techniques including, liquid delivery chemical vapor deposition (LDCVD), and digital or atomic layer chemical vapor deposition (ALCVD) and provide background and assistive information with respect to the practice of the present invention.

In general, the silicon precursor composition(s) and method(s) of making such precursor composition(s) of the instant invention may be formulated to comprise, consist of, or consist essentially of any appropriate components herein disclosed, and such silicon precursor compositions of the invention may additionally, or alternatively, be formulated to be devoid, or substantially free, of any components taught to be necessary in prior art formulations that are not necessary to the achievement of the objects and purposes of the invention hereunder.

The compositions of the present invention are useful in a number of applications. For example, the compositions may be used in the formation of silicon nitride barrier layers, low dielectric constant thin films and gate dielectric thin films in a semiconductor integrated circuit. To form such integrated circuits, a semiconductor substrate may have a number of dielectric and conductive layers formed on and/or within the substrate.

As used herein, the semiconductor substrate may include a bare substrate or a substrate having any number of layers formed thereon and the term "thin film" refers to a material layer having a thickness of less than about 1000 microns.

In one embodiment, the present invention relates to a method of synthesizing an aminosilane source reagent composition, by reacting an aminosilane precursor compound with an amine source reagent compound in a solvent medium comprising at least one activating solvent component, to yield an aminosilane source reagent composition having reduced halide content as compared to the existing commercial precursors. Preferably the aminosilane source reagent compound comprises less than 1000 ppm halide, more preferably less than 500 ppm and most preferably less than 10 ppm halide.

Aminosilane precursor compounds useful in the synthetic process of the instant invention must have reactive leaving groups, such as H and/or halogen. In one embodiment, aminosilane precursor compounds useful in the instant invention include but are not limited to, silicon halides, alkylsilanes and other aminosilanes. Preferably, the aminosilane precursor compound is a silicon halide compound comprising a composition selected from the group consisting of:

(4)

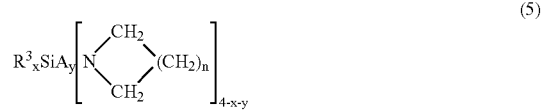

(5)

wherein $R^3$ is selected from the group consisting of hydrogen, $C_1$–$C_4$ alkyl, and $C_1$–$C_4$ alkoxy; x is from 0 to 3; Si is silicon; A is halogen; y is from 1 to 4; N is nitrogen; each of $R^1$ and $R^2$ is same or different and is independently selected from the group consisting of H, aryl, perfluoroaryl, $C_1$–$C_8$ alkyl, and $C_1$–$C_8$ perfluoroalkyl; and n is from 1–6. Preferably, A is Cl.

The amine source reagent compounds useful in the synthetic process of the instant invention, include but are not limited to amines having a composition selected from the group consisting of

(6)

(7)

wherein B is selected from the group consisting of H, Li, Na, K, Zn and MgBr; N is nitrogen; $R^1$ and $R^2$ are same or different and each is independently selected from the group consisting of H, aryl, perfluoroaryl, $C_1$–$C_8$ alkyl, and $C_1$–$C_8$ perfluoroalkyl; and n is from 1–6. Preferably, $R^1$ and $R^2$ are methyl and/or ethyl.

Activating solvent components useful in the present invention include but are not limited to Lewis base compounds such as ethers and amines. More specifically, ethereal solvents useful in the present invention include but are not limited to, diethyl ether, tetrahydrofuran (THF), ethylene glycol dimethyl ether (glyme), diethylene glycol dimethyl ether (diglyme), 1,4-dioxane, tetraethylene glycol dimethyl ether (tetraglyme), 1,4,7,10-tetraoxacyclododecane (12-Crown-4), 1,4,7,10,13-pentaoxacyclopentadecane (15-Crown-5), and 1,4,7,10,13,16-hexaoxacyclooctadecane (18-Crown-6); and amine solvents useful in the present invention include but are not limited to tertiary amines selected from the group consisting of, pentamethyldiethylenetriamine (PMDETA), tetramethylethylene-diamine (TMEDA), Triethylamine; (TEA), Diazabicycloun-decene (DBU), Tri-n-butylamine (TNBA), and tetraethylethylenediamine (TEDA).

Many of the amine source reagent compounds useful in the present invention exist as oligomers. The oligomer prevents substitution of all reactive leaving groups (i.e., halides) on the aminosilane precursor compound, since the oligomer is not as soluble in many solvents and hence, not as reactive as its corresponding monomer. However, in the presence of a polar activating solvent, the oligomers are solvated into monomeric species, thus providing the impetus for the amine-leaving group substitution to occur.

Non-polar solvents useful in the present invention include but are not limited to alkanes, alkenes, alkynes and aromatic hydrocarbons.

In a further embodiment, the present invention relates to a method of synthesizing an aminosilane source reagent composition, comprising the steps of:

(1) combining an aminosilane precursor compound with an amine source reagent compound in a solvent system comprising at least one non-polar solvent, for a period of time sufficient to provide for partial substitution of at least one halide on the aminosilane precursor compound by an amine component, to produce a reaction mixture comprising a partially substituted aminosilane component and an unreacted amine component;

(2) removing the non-polar solvent from the reaction mixture by vacuum evaporation;

(3) adding an activating polar solvent to the partially substituted aminosilane component and the unreacted amine component of the reaction mixture of step (1) to at least partially activate the unreacted amine component;

(4) continuing the reaction of step (3) for a period of time sufficient to provide for essentially stoichiometric substitution of at least one halide on the aminosilane precursor compound by an amine component.

In one embodiment, the present invention relates to a method of synthesizing an aminosilane source reagent composition, by reacting an aminosilane precursor compound with an amine source reagent compound in a solvent system comprising at least one activating solvent component in an amount equal to at least one equivalent of the amine source reagent compound, to yield an aminosilane precursor having reduced halide content as compared to existing commercial precursors.

In a preferred embodiment of the synthetic method of the instant invention, the aminosilane precursor compound is combined with an amount of the amine source reagent compound that is in excess of at least one equivalent of the amine source reagent compound as shown in the following non limiting generic example:

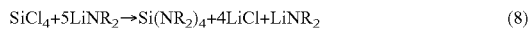

SiCl$_4$+5LiNR$_2$→Si(NR$_2$)$_4$+4LiCl+LiNR$_2$     (8)

The synthetic method of the instant invention, is not limited to the specific examples disclosed herein, but rather includes any combination of solvents in any order with the requirement that at least one solvent component comprise a polar activating component.

In a further embodiment, an aminosilane source reagent composition is formed by a synthetic process comprising the steps:

(1) combining an aminosilane precursor compound (e.g. SiCl$_4$) with excess amine source reagent compound that is equal to at least one molar equivalent of the amine source reagent compound (e.g., 5LiNR$_2$), in a solvent system comprising at least one non-polar solvent, such as hexanes, for a period of time sufficient to provide for partial substitution of at least one reactive leaving group on the aminosilane precursor compound, to produce a reaction mixture comprising a partially substituted aminosilane component and an unreacted amine component;

(2) removing the non-polar solvent from the reaction mixture by vacuum evaporation;

(3) adding a polar solvent, such as tetraglyme, to the partially substituted aminosilane component and the unreacted amine component of the reaction mixture of step (1) to at least partially activate the unreacted amine component;

(4) continuing the reaction of step (3) for a period of time sufficient to provide for essentially stoichiometric substitution of all reactive leaving groups on the silicon halide source reagent compound by an amine component.

The period of time required for reactions to complete and the temperature at which they are run, are parameters readily determined by those skilled in the art. Such determinations are based on parameters such as pressure, concentration, mixing speed etc.

In one embodiment, the reaction mixture of step (1) as outlined hereinabove, wherein the aminosilane precursor compound is combined with the amine source reagent compound, should be carried out at a temperature that is in the range of from about −30° C. to room temperature and a pressure that is about one atmospheric pressure. Preferably the combination of the compounds is carried out at a temperature of ±0° C. and a pressure that is about one atm.

In a further embodiment, the reaction mixture of step (3) as outlined hereinabove, wherein the aminosilane precursor compound having partially substituted leaving groups, is combined with the amine source reagent compound, and the polar activating solvent, should be carried out at a temperature that is in the range of from about 0° C. to 100° C. at ambient pressure. Preferably the reaction of step (3) is carried out a temperature that is ±60° C. at an ambient pressure.

The aminosilane source reagent compositions synthesized in the aforementioned procedures, are crude product and must be isolated and purified. Such isolation and purification methods are readily available and known to those skilled in the instant art. Preferably the crude aminosilane source reagent composition is separated from the by-product by filtration or decantation and preferably the separated aminosilane source reagent composition is further purified by distillation to produce an aminosilane source reagent composition having a halogen level of less than 1000 ppm, preferably less than 500 ppm and most preferably less than 10 ppm.

The aminosilane source reagent compositions of the present invention, when utilized in a CVD process to deposit silicon containing thin films on a substrate, result in silicon containing thin films having very little or no halide impurity.

In one embodiment, the present invention relates to silicon precursors made by reacting an aminosilane precursor compound with an amine source reagent compound in a solvent medium comprising at least one activating solvent component, to yield an aminosilane source reagent composition having a halogen content that is less than 1000 ppm, said aminosilane source reagent composition selected from the group consisting of:

$$R^3{}_xSiA_y(NR^1R^2)_{4-x-y} \text{ and} \qquad (2)$$

$$R^3{}_xSiA_y\left[N\begin{array}{c}CH_2\\CH_2\end{array}(CH_2)_n\right]_{4-x-y} \qquad (3)$$

wherein $R^3$ is selected from the group consisting of hydrogen, $C_1$–$C_4$ alkyl, and $C_1$–$C_4$ alkoxy; x is from 0 to 3; Si is silicon; A is halogen; Y is from 0 to 3; N is nitrogen; each of $R^1$ and $R^2$ is same or different and is independently selected from the group consisting of H, aryl, perfluoroaryl, $C_1$–$C_8$ alkyl, and $C_1$–$C_8$ perfluoroalkyl; and n is from 1–6.

In a further embodiment, the present invention relates to novel, stable aminosilane source reagent compositions having formula:

$$R^3{}_xSiA_y(NR^1R^2)_{4-x-y} \qquad (2)$$

wherein $R^3$ is selected from the group consisting of hydrogen, $C_1$–$C_4$ alkyl, and $C_1$–$C_4$ alkoxy; x is from 0 to 3, A is Cl, y is from 0 to 3; $R^1$ is methyl; and $R^2$ is ethyl.

In a preferred embodiment, the aminosilane source reagent compounds useful for depositing a silicon containing thin film on a substrate include but are not limited to: $Si(NMe_2)_3Cl$, $Si(NEt_2)_2Cl_2$, $Si(NMe_2)_4$, $Si(NEt_2)_4$ and $Si(NMeEt)_4$, $HSi(NEt_2)_3$, $HSi(NEtMe)_3$.

The invention in one embodiment relates to a CVD precursor for forming a silicon containing thin film on a substrate, such precursor composition including at least one aminosilane source reagent composition.

The aminosilane source reagent compositions of the instant invention are useful for producing silicon containing thin films, including but not limited to silicon nitride thin films, $SiO_2$ dielectric thin films, doped $SiO_2$ dielectric thin films, low dielectric constant thin films and metal silicon-oxy-nitride thin films.

In one embodiment, the silicon precursor composition of the instant invention is used in combination with a dopant precursor to deposit a doped dielectric $SiO_2$ thin film. Preferably the dopant precursor comprises a metalloamide source reagent composition.

In a still further embodiment, the instant invention relates to a silicon precursor composition used in combination with a dopant precursor to deposit a metal silicate thin film, wherein the silicon precursor is an aminosilane source reagent composition selected from the group consisting of $$R^3{}_xSiA_y(NR^1R^2)_{4-x-y}; \text{ and} \qquad (2)$$

$$R^3{}_xSiA_y\left[N\begin{array}{c}CH_2\\CH_2\end{array}(CH_2)_n\right]_{4-x-y} \qquad (3)$$

wherein $R^3$ is selected from the group consisting of hydrogen, $C_1$–$C_4$ alkyl, and $C_1$–$C_4$ alkoxy; x is from 0 to 3; Si is silicon; A is halogen; Y is from 0 to 3; N is nitrogen; each of $R^1$ and $R^2$ is same or different and is independently selected from the group consisting of H, aryl, perfluoroaryl, $C_1$–$C_8$ alkyl, and $C_1$–$C_8$ perfluoroalkyl; and n is from 1–6; and the dopant precursor is a metalloamide source reagent composition selected from the group consisting of:

$$M(NR^1R^2)_x; \text{ and} \qquad (9)$$

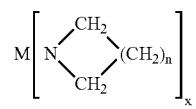

$$M\left[N\begin{array}{c}CH_2\\CH_2\end{array}(CH_2)_n\right]_x \qquad (10)$$

wherein, M is selected from the group consisting of: Zr, Hf, Y, La, Lanthanide series elements, Ta, Ti, Al; N is nitrogen; each of $R^1$ and $R^2$ is same or different and is independently selected from the group consisting of H, aryl, perfluoroaryl, $C_1$–$C_8$ alkyl, $C_1$–$C_8$ perfluoroalkyl, alkylsilyl; x is the oxidation state on metal M; and n is from 1–6.

In a preferred embodiment, M is Zr or Hf, and $R^1$ and $R^2$ are methyl and/or ethyl. In a more preferred embodiment, the metalloamide source reagents useful for depositing dielectric thin films on a substrate include but are not limited to, compounds of the formula $M(NMe_2)_x$, $M(NEt_2)_x$, $M(NMeEt)_x$ Examples of metalloamide source reagent compositions, which may be usefully employed in the present invention include, without limitation, $Zr(NMe_2)_4$, $Zr(NMeEt)_4$, $Zr(NEt_2)_4$, $Ta(NEt_2)_5$, $Ta(NMe_2)_5$, $Ta(NMeEt)_5$, $Zr(NiPr_2)_4$, $Zr(NMe_2)_2(NPr_2)_2$, $Zr(NC_6H_{12})_4$, $Zr(NEt_2)_2(NPr_2)_2$, $Hf(NEt_2)_4$, $Hf(NMe_2)_4$, $Hf(NMeEt)_4$, $La(NMe_2)_3$, $La(NEt_2)_3$, $La(NMeEt)_3$, $Al(NMe_2)_3$, $Al(NEt_2)_3$, $Y(NMe_2)_3$, $Y(NEt_2)_3$, $Y(NMeEt)_3$, $Ti(NMe_2)_4$, $Ti(NEt_2)_4$, $Ti(NMeEt)_4$, $Ta(NMe_2)_5$, $Ta(NEt_2)_5$, wherein Me represents methyl, Et represents ethyl, Pr represents propyl, and iPr represents isopropyl. Preferred metalloamide source reagent compounds useful in the present invention include $Zr(NMe_2)_4$, $Zr(NEt_2)_4$, $Hf(NEt_2)_4$ and $Hf(NMe_2)_4$.

In a specific embodiment, the metalloamide source reagent compound useful in the present invention may comprise an oligomer, i.e. $Al_2(\mu-NMe_2)_2(NMe_2)_4$.

In a further embodiment, the present invention relates to a CVD precursor composition for forming a silicon containing thin film on a substrate, said precursor composition made by reacting an aminosilane precursor compound with an amine source reagent compound in a solvent medium comprising at least one activating solvent component, to yield an aminosilane source reagent composition having a halogen content that is less than 1000 ppm, said precursor composition including at least one aminosilane source reagent composition selected from the group consisting of:

$$R^3{}_xSiA_y(NR^1R^2)_{4-x-y} \text{ and} \qquad (2)$$

$$R^3{}_xSiA_y\left[N\begin{array}{c}CH_2\\CH_2\end{array}(CH_2)_n\right]_{4-x-y} \qquad (3)$$

wherein $R^3$ is selected from the group consisting of hydrogen, $C_1$–$C_4$ alkyl, and $C_1$–$C_4$ alkoxy; x is from 0 to 3; Si is silicon; A is halogen; Y is from 0 to 3; N is nitrogen; each of $R^1$ and $R^2$ is same or different and is independently selected from the group consisting of H, aryl, perfluoroaryl, $C_1$–$C_8$ alkyl, and $C_1$–$C_8$ perfluoroalkyl; and n is from 1–6.

In a still further embodiment, the present invention relates to a CVD precursor composition for forming a silicon containing thin film on a substrate, such precursor composition including at least one aminosilane source reagent composition selected from the group for forming a silicon containing thin film on a substrate; and at least one metalloamide source reagent composition selected from the group consisting of:

$$M(NR^1R^2)_x \text{ and} \quad (9)$$

(10)

wherein M is selected from the group consisting of: Zr, Hf, Y, La, Lanthanide series elements, Ta, Ti, Al; N is nitrogen; each of $R^1$ and $R^2$ is same or different and is independently selected from the group consisting of H, aryl, perfluoroaryl, $C_1$–$C_8$ alkyl, $C_1$–$C_8$ perfluoroalkyl, alkylsilyl; x is the oxidation state on metal M; and n is from 1–6. Preferably, $R^1$ and $R^2$ of the aminosilane and metalloamide source reagent compositions are methyl and/or ethyl.

In one embodiment, the silicon CVD precursor composition of the present invention is used to deposit a metal silicate gate dielectric thin film wherein the silicon precursor is suitably used in combination with at least one dopant precursor, to yield the product metal silicate film. The dopant precursor may advantageously comprise a metalloamide source reagent composition as described herein or may alternatively comprise an alternative dopant source reagent composition as known to those skilled in the art, to deposit metal silicate thin films, (e.g. metal beta-diketonates, metal alkoxides, and metal carboxylates).

By utilizing a precursor composition including at least one aminosilane source reagent composition and at least one metalloamide source reagent composition to produce a metal silicate dielectric thin film on a substrate, with the metalloamide source reagent composition containing at least part of the metal to be incorporated in the product dielectric metal silicate film, and the aminosilane source reagent compound containing at least part of the silicon to be incorporated in the product dielectric metal silicate film, it is possible by selection of the proportions of such respective compounds to correspondingly vary the stoichiometric composition (metal/silicon ratio) of the metal silicate dielectric film, to obtain a desired character of structural and performance properties in the product film. The relative proportions of the at least one aminosilane source reagent composition and the metalloamide source reagent composition relative to one another are employed to controllably establish the desired $M_x/Si_{1-x}$ ratio in the deposited silicate thin films, wherein $M_x/Si_{1-x}$ is from about 0.01 to 10. The exact composition will be a trade off between high Si films, which prevent crystallization during subsequent high temperature processing, and high M films, which have higher dielectric constant (lower EOT).

In one embodiment, the silicon CVD precursor composition of the present invention is used to deposit a silicon nitride barrier layer, wherein the silicon precursor is suitably used in combination with $NH_3$, to yield the product silicon nitride film. The CVD precursor composition may be used in combination with silicon and/or nitrogen sources as readily known to those skilled in the art, to deposit silicon nitride thin films, (e.g., ammonia).

In a further embodiment, the present invention relates to stable solutions for chemical vapor deposition (CVD) of silicon-containing thin films of varying types, including silicon nitride, silicon dioxide and doped silicon dioxide films (when a dopant co-precursor is utilized), wherein the stable solution comprises at least one aminosilane source reagent composition and at least one solvent component, in which the aminosilane source reagent composition is soluble or suspendable. Accordingly, the aminosilane source reagent composition and the at least one solvent component are combined to produce a precursor solution mixture for depositing a silicon containing thin film on the substrate.

In a further embodiment, the present invention relates to a CVD multi-component, single source precursor composition useful for forming a metal silicate dielectric thin film on a substrate, such precursor composition including at least one aminosilane source reagent composition as described hereinabove, at least one metalloamide source reagent composition as described hereinabove and a solvent medium in which the aminosilane source reagent composition and the metalloamide source reagent composition are soluble or suspendable, wherein the aminosilane source reagent composition, the metalloamide source reagent composition, and the solvent medium are combined to produce a chemically compatible, single source solution mixture for depositing a silicon containing dielectric thin film on the substrate.

Providing a precursor composition in liquid (i.e., neat solution or suspension) form facilitates rapid volatilization (i.e., flash vaporization) of the source reagent composition and transport of the resultant precursor vapor to a deposition locus such as a CVD reaction chamber. The aminosilane and metalloamide source reagent compositions of the present invention are chosen to provide a degenerate sweep of ligands, to eliminate ligand exchange and to provide a robust precursor delivery, gas-phase transport and CVD process.

The precursor compositions of the present invention may comprise any suitable solvent medium that is compatible with the aminosilane and optionally the metalloamide source reagent compositions contained therein. The solvent medium in such respect may comprise a single solvent component, or alternatively a mixture of solvent components. Illustrative solvent media that may be variously usefully employed include ethers, glymes, tetraglymes, amines, polyamines, aliphatic hydrocarbon solvents, aromatic hydrocarbon solvents, cyclic ethers, and compatible combinations of two or more of the foregoing. A particularly preferred solvent species useful in the practice of the present invention is octane. The percentage of the precursor in the solution may range from 0.1 to 99.99% by weight, based on the total weight of the solution.

The silicon precursor compositions of the invention may be deposited on a wafer or other substrate by use of a CVD system, such systems being well known in the semiconductor fabrication art. Preferred CVD systems include low-pressure CVD systems.

In a further embodiment the present invention relates to a method for forming a silicon containing thin film on a substrate by chemical vapor deposition, such method including the steps of:

(1) vaporizing a precursor composition comprising at least one aminosilane source reagent composition made by reacting an aminosilane precursor compound with an amine source reagent compound in a solvent medium comprising at least one activating solvent component, to yield an aminosilane source reagent composition having a halogen content that is less than 1000 ppm, wherein said aminosilane source reagent composition is selected from the group consisting of:

wherein $R^3$ is selected from the group consisting of hydrogen, $C_1$–$C_4$ alkyl, and $C_1$–$C_4$ alkoxy; x is from 0 to 3; Si is silicon; A is halogen; Y is from 0 to 3; N is nitrogen; each of $R^1$ and $R^2$ is same or different and is independently selected from the group consisting of H, aryl, perfluoroaryl, $C_1$–$C_8$ alkyl, and $C_1$–$C_8$ perfluoroalkyl; and n is from 1–6;

(2) transporting such precursor vapor into a chemical vapor deposition zone containing a substrate, optionally using a carrier gas to effect such transport;

contacting the precursor vapor with a substrate in such chemical vapor deposition zone, at elevated temperature to deposit a corresponding silicon containing thin film.

A wide variety of CVD process conditions may be utilized for chemical vapor deposition employing the compositions of the present invention. Typical liquid delivery MOCVD process conditions may include substrate temperature ranges of 160–300° C., with about 170° C. to about 250° C. being more typical; vaporizer temperature ranges may be from about 50° C. to about 150° C., with about 60° C. to about 100° C. being more typical; pressure ranges are generally from about 0.05 to about 20 Torr (and most preferably from about 0.1 to about 5 Torr), with a range of about 0.2 to about 0.5 Torr being more typical; and inert gas flows of helium or argon of from about 25–750 sccm (and most preferably from about 50 to about 200 sccm), at a temperature approximately the same as the vaporizer. In some cases, a co-reactant may be introduced (i.e., water, alcohol or hydrogen forming gas) to facilitate the film growth process.

The compositions of the present invention are not limited in respect of their use with the aforementioned low-pressure CVD deposition tools, however, and other CVD tools, for example PECVD tools, or other deposition tools, may be utilized.

In one embodiment the aminosilane source reagent compositions of the instant invention may used in an atomic layer chemical vapor deposition method, wherein the aminosilane source reagent composition is vaporized and introduced into a chemical vapor deposition chamber comprising a substrate, in a sequential or "pulsed" deposition mode, during which time, extremely co-reactive gases may be employed, such as ozone, water vapor or reactive alcohols, that might normally be expected to produce deleterious deposition effects on the CVD process (i.e., gas phase particle formation).

In a further embodiment, the atomic layer chemical vapor deposition method of the present invention, may further comprise a metalloamide precursor vapor that may be simultaneously co-pulsed and co-deposited with the silicon precursor vapor, on a substrate. Alternatively, the aminosilane precursor vapor may be deposited on a substrate in a sequential pulsing method, wherein the aminosilane compound alternates pulses with the metalloamide compound. The dielectric thin films are built up by introducing short bursts of gases in cycles.

In a further embodiment, a co-reactant may be used in a pulsed or atomic layer chemical vapor deposition method, wherein the metalloamide precursor and/or aminosilane precursor vapor is separated from the co-reactant by time in the pulse track. The co-reactant may be utilized to facilitate the decomposition of the precursor on a substrate, within a desired temperature regime and to produce carbon-free dielectric thin-films. As an example, the use of water vapor may be utilized to induce a lower decomposition temperature of the aminosilane precursor vapor, which in some instances has been found to be stable in oxidizing environments such as $N_2O$.

The specific nature of the pulse track and number of cycles may be varied. In a typical ALCVD process, a cycle lasts from 1–5 seconds. The following non-limiting examples demonstrate various pulse tracks defining precursor(s) and co-reactant(s) that may be successfully used to deposit the dielectric thin films of the present invention:

example track 1–(metalloamide/purge (inert)/co-reactant+$N_2O$/purge (inert))n cycles;

example track 2–(metalloamide+aminosilane/purge (inert)/$N_2O$/purge (inert))n cycles;

example track 3–(metalloamide+co-reactant $N_2O$/co-reactant water vapor/purge (inert))n cycles;

example track 4–(metalloamide+co-reactant $N_2O$/aminosilane/co-reactant water vapor/purge (inert))n cycles.

wherein n is an integer number, typically ranging from 10 to 100, and different co-reactants have different oxidizing potentials.

The compositions of the present invention may be delivered to the CVD reactor in a variety of ways. For example, a liquid delivery system may be utilized. Such systems generally include the use of liquid MFCs (mass flow controllers). An exemplary liquid delivery system that may be used is the ATMI Sparta 150 Liquid Delivery System (commercially available from ATMI, Inc., Danbury, Conn.).

Liquid delivery systems generally meter a desired flow rate of the precursor composition in liquid form to the CVD process tool. At the process tool chamber, or upstream thereof, the liquid may be vaporized through use of a vaporizer. Such vaporizers may utilize thermal heating, acoustics, ultrasound and high flow nebulizers. Further descriptions of liquid delivery systems are contained in U.S. Pat. Nos. 5,204,314; 5,362,328; 5,536,323; and 5,711,816, the disclosures of which are hereby expressly incorporated herein by reference in their entireties.

In the practice of the present invention utilizing liquid delivery, the silicon precursor species, if of solid or liquid form at ambient conditions, may be dissolved or suspended in a compatible solvent medium as more fully described in U.S. Pat. No. 5,820,664 issued Oct. 13, 1998 for "Precursor Compositions For Chemical Vapor Deposition, And Ligand Exchange Resistant Metal-Organic Precursor Solutions Comprising Same," the disclosure of which is hereby incorporated herein in its entirety by reference.

The precursors of the present invention may be deposited using any chemical vapor deposition system known in the art. A preferred liquid delivery MOCVD System is described in U.S. Pat. No. 5,204,314, issued Apr. 20, 1993, for "Method for Delivering an Involatile Reagent in Vapor Form to a CVD Reactor," the disclosure of which is hereby incorporated herein in its entirety by reference.

In liquid delivery CVD, the source liquid may comprise the source reagent compound(s) if the compound or complex is in the liquid phase at ambient temperature (e.g., room temperature, 25° C.) or other supply temperature from which the source reagent is rapidly heated and vaporized to form precursor vapor for the CVD process. Alternatively, if the source reagent compound or complex is a solid at ambient or the supply temperature, such compound or complex can be dissolved or suspended in a compatible solvent medium therefore to provide a liquid phase composition that can be submitted to the rapid heating and vaporization to form precursor vapor for the CVD process. The precursor vapor resulting from the vaporization then is transported, optionally in combination with a carrier gas (e.g., He, Ar, $H_2$, $O_2$, etc.), to the chemical vapor deposition reactor where the vapor is contacted with a substrate at elevated temperature to deposit material from the vapor phase onto the substrate or semiconductor device precursor structure positioned in the CVD reactor.

The precursor liquid may be vaporized in any suitable manner and with any suitable vaporization means to form corresponding precursor vapor for contacting with the elevated temperature substrate on which the dielectric film is to be formed. The vaporization may for example be carried out with a liquid delivery vaporizer unit of a type as commercially available from Advanced Technology Materials, Inc. (Danbury, Conn.) under the trademark SPARTA and VAPORSOURCE II, in which precursor liquid is discharged onto a heated vaporization element, such as a porous sintered metal surface, and flash vaporized. The vaporizer may be arranged to receive a carrier gas such as argon, helium, etc. and an oxygen-containing gas may be introduced as necessary to form the dielectric thin film. The precursor vapor thus is flowed to the chemical vapor deposition chamber and contacted with the substrate on which the dielectric film is to be deposited. The substrate is maintained at a suitable elevated temperature during the deposition operation by heating means such as a radiant heating assembly, a susceptor containing a resistance heating element, microwave heat generator, etc. Appropriate process conditions of temperature, pressure, flow rates and concentration (partial pressures) of metal and silicon components are maintained for sufficient time to form the dielectric film at the desired film thickness, (i.e., in a range of from about 2 nanometers to about 1000 micrometers), and with appropriate dielectric film characteristics.

The step of vaporizing the source reagent compounds of the present invention is preferably carried out at a vaporization temperature in the range of from about 50° C. to about 300° C. Within this narrow range of vaporization temperature, the metalloamide and aminosilane source reagent compounds are effectively vaporized with a minimum extent of premature decomposition.

In the optional use of a carrier gas in the practice of the present invention, for transporting the vaporized source reagent composition into the chemical vapor deposition zone, suitable carrier gas species include gases that do not adversely affect the dielectric film being formed on the substrate. Preferred gases include argon, helium, krypton or other inert gas, with argon gas generally being most preferred. In one illustrative embodiment, argon gas may be introduced for mixing with the vaporized source reagent composition at a flow rate of about 100 standard cubic centimeters per minute (sccm).

Oxidizing gases useful for the broad practice of the present invention include, but are not limited to, $O_2$, $N_2O$, NO, $H_2O$ and $O_3$, More preferably, the oxidizer used comprises $N_2O$.

The deposition of the silicon containing thin films of the present invention are preferably carried out under an elevated deposition temperature in a range of from about 250° C. to about 750° C.

The use of the compositions disclosed herein is not limited to liquid delivery systems, and any method, which adequately delivers the composition to the process tool is satisfactory. Thus, for example, bubbler-based delivery systems may be utilized, but are not preferred. In such systems, an inert carrier gas is bubbled through the precursor composition (typically in liquid form above its melting point). The resulting gas, which is wholly or partially saturated with the vapor of the composition, is provided to the CVD tool.

Here and throughout this disclosure, where the invention provides that at least one aminosilane source reagent composition is present in a composition or method, the composition or method may contain or involve additional aminosilane and/or other compounds.

EXAMPLES

Experiment 1

Figure 2A:
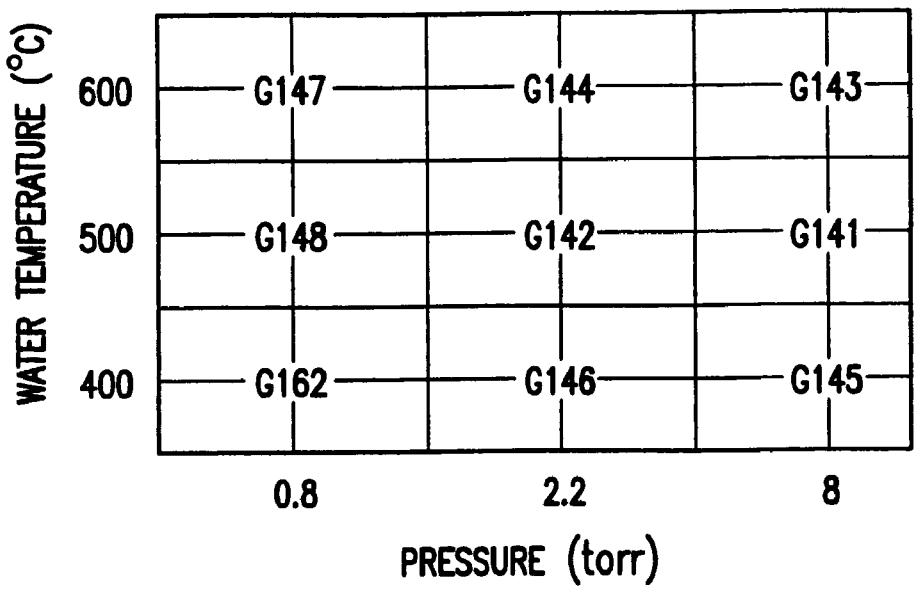
FIGS. 2A and 2B show a limited pressure-temperature matrix for Si(N(C$_2$H$_5$)$_2$)$_2$Cl$_2$(bis(diethyl-amino)dichlorosilane), and Si(N(CH$_3$)$_2$)$_3$Cl (tris(dimethyl-amino)chlorosilane in N$_2$O.
Figure 2B:
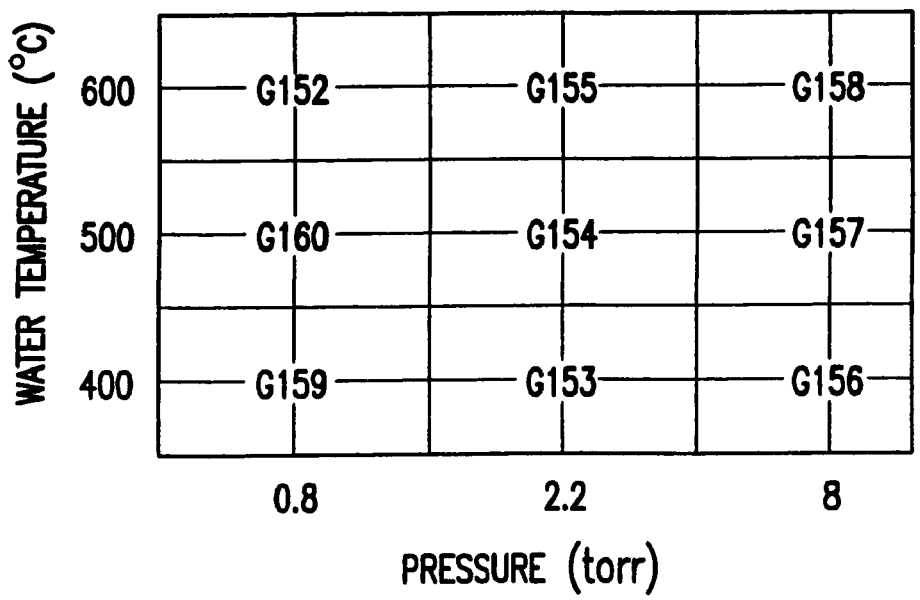

Silica films were grown with the silicon precursors listed in Table I, $Si(NMe_2)_3Cl$ and $Si(NEt_2)_2Cl_2$. Precursor solutions were prepared at 0.1M Si in octane. Substrates of (100) Si were prepared with an SC1 treatment followed by dilute HF to remove any native $SiO_2$. The generic process conditions for the experiments are shown in Table II. Results from the growth of hafnia films encouraged the inventors to center initial experiments on growth in an $N_2O$ atmosphere although growth in $O_2$ or other oxidizer could be used at temperatures at or below 500° C. A limited pressure-temperature matrix was performed for each Si precursor using the $N_2O$ ambient as shown in FIGS. 2A and 2B.

TABLE I

Precursors used for film deposition.

| | | |
|---|---|---|
| (Bis(diethyl-amino)dichlorosilane) | $Si(N(C_2H_5)_2)_2Cl_2$ | |
| (Tris(dimethyl-amino)chlorosilane) | $Si(N(CH_3)_2)_3Cl$ | |
| Tetrakis(diethyl-amino)hafnium | $Hf(N(C_2H_5)_2)_4$ | TDEAHf |
| Tetrakis(dimethyl-amino)hafnium | $Hf(N(CH_3)_2)_4$ | TDMAHf |

TABLE II

Generic process conditions

| | |
|---|---|
| Precursor solution | 0.10M in octane |
| Precursor solution delivery rate | 0.10 ml/min |
| Vaporization Temperature | 150° C. |
| Run time | 10 minutes |
| Carrier gas | 100 sccm Ar |
| Heating and Cooling process gas | 500 sccm Ar |
| Run time process gas | 400 sccm $N_2O$ |
| Pressure | 0.8, 2.2, or 8.0 Torr |
| Temperature | 400–650° C. wafer surface |

From NMR studies of precursor compatibility, it was shown that $Si(NEt_2)_2Cl_2$ is compatible with TDEAHf in solution, with any ligand exchange being degenerate. $Si(NMe_2)_3Cl$ is compatible with both TDEAHf and TDMAHf. A solution of 0.05M TDEAHf: 0.05M $Si(NEt_2)_2Cl_2$ was produced by mixing the two 0.1M solutions. This mixture was used to grow films over the entire matrix of process conditions.

Film thickness was measured using single-wavelength ellipsometry at 70° incidence angle, and XRF. For $SiO_2$ deposition, all films were less than 30 Å thick, so an index of refraction could not be measured accurately. Film thickness was assigned based on an assumed index of refraction, n=1.46, typical of high quality thermal oxide. For $HfO_2$, the XRF was calibrated by assuming the X-ray efficiencies were equivalent to $TaO_{2.5}$, for which standards that been measured by RBS. The Hf:Si composition was estimated by assuming that both are fully oxidized and fully dense. The ellipsometric thickness not accounted for by $HfO_2$ was assigned to $SiO_2$, and composition was calculated from these two thicknesses.

Results

Figure 3:
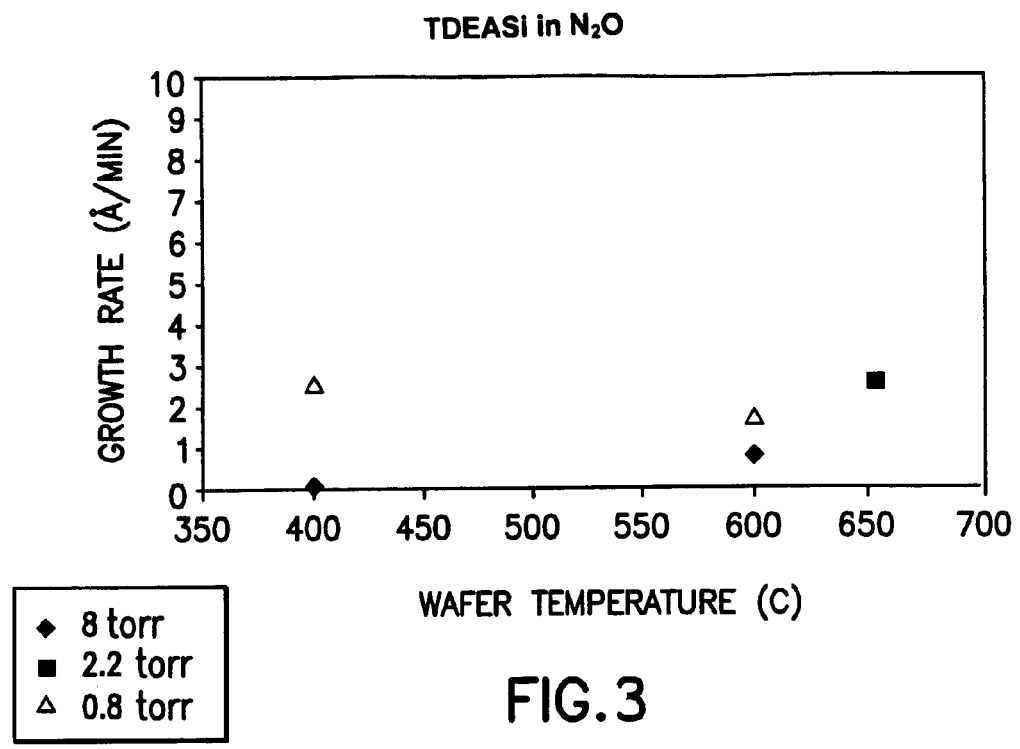
FIG. 3 shows the growth rate of silica from Si(N(C$_2$H$_5$)$_2$)$_2$Cl$_2$ (Bis(diethyl-amino)dichlorosilane) in N$_2$O ambient.
Figure 4:
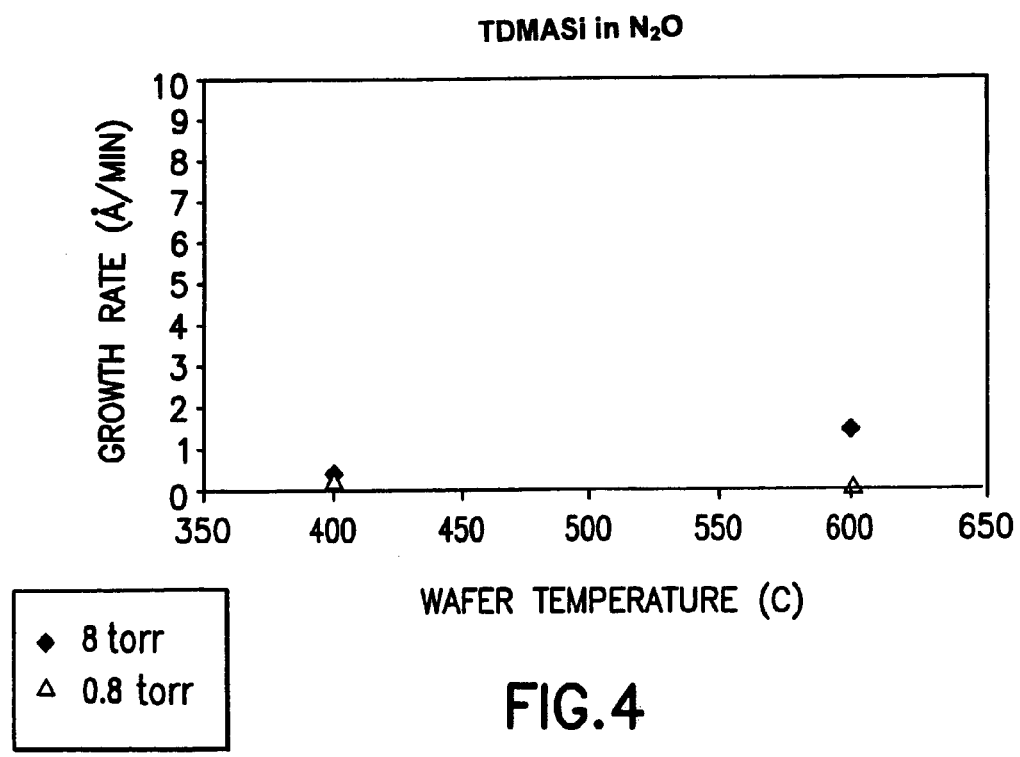
FIG. 4 shows the growth rate of silica from Si(N(CH$_3$)$_2$)$_3$Cl (Tris(dimethyl-amino)chlorosilane in N$_2$O ambient.

Growth rates of $SiO_2$ were less than 3 Å/min under all conditions as shown in FIG. 3 and FIG. 4. There is some indication that the $Si(NEt_2)_2Cl_2$ may form silica films a little bit more readily, however, none of the growth rates are sufficient for the two precursors under the instant conditions.

Figure 5:
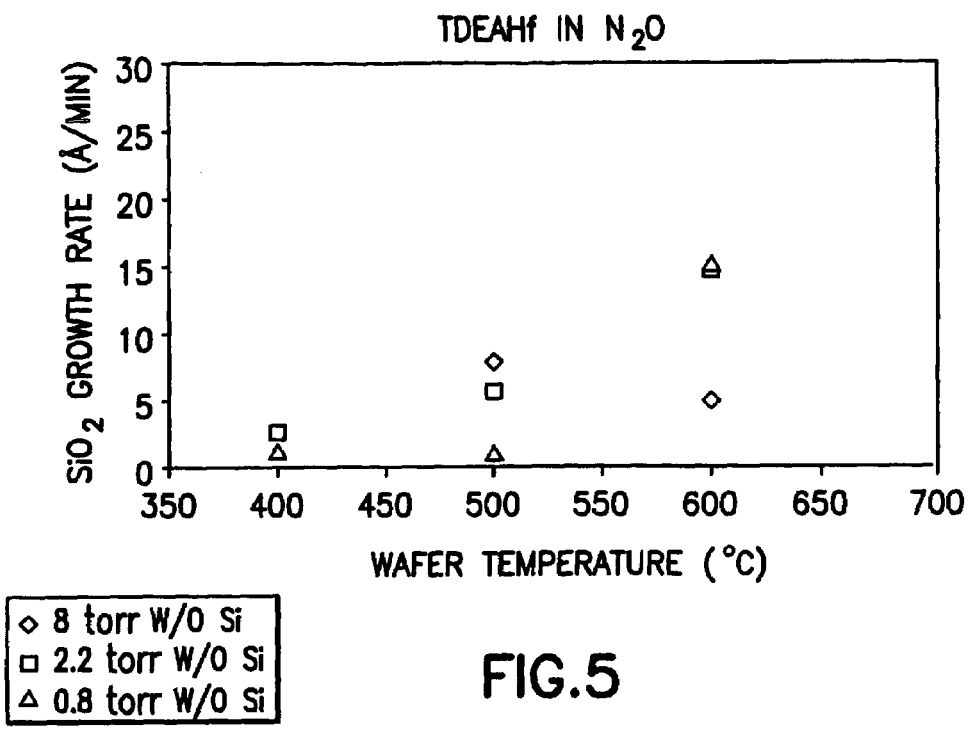
FIG. 5 shows the growth rate of SiO$_2$ under a HfO$_2$ film with no silicon precursor present.
Figure 6:
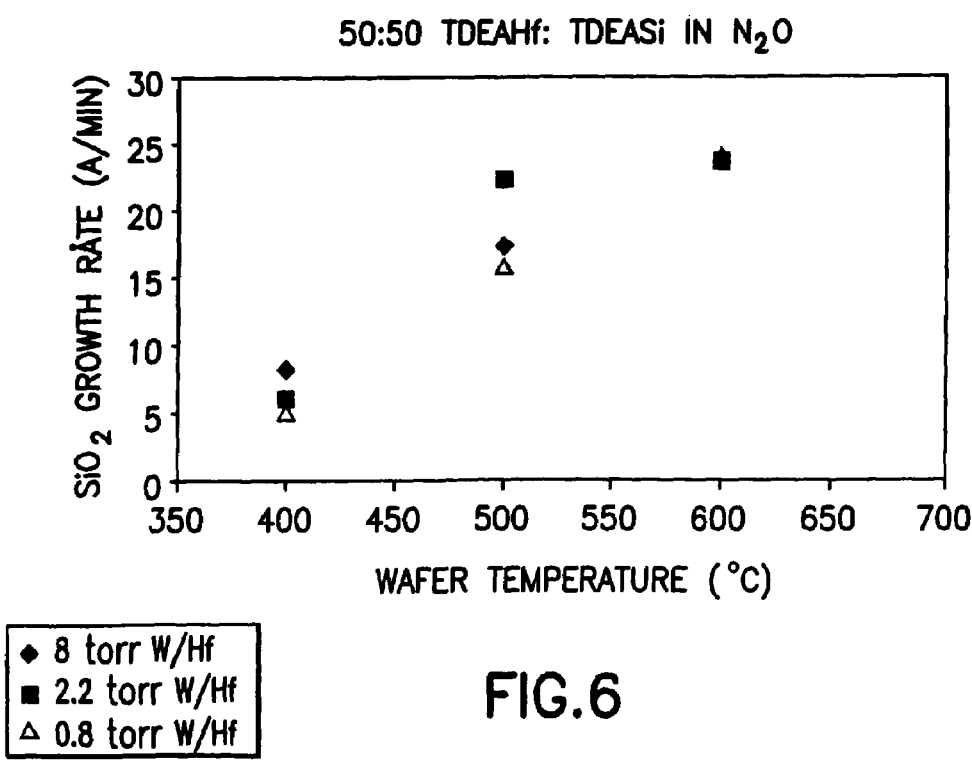
FIG. 6 shows the growth rate of SiO$_2$ from Si(N(C$_2$H$_5$)$_2$)$_2$Cl$_2$ (Bis(diethyl-amino)dichlorosilane when co-deposited with HfO$_2$ from Hf(N(C$_2$H$_5$)$_2$)$_4$ (Tetrakis(diethyl-amino) hafnium in N$_2$O ambient.

The growth of $SiO_2$ with only the TDEAHf, as measured by the subtraction of ellipsometric thickness from XRF thickness (shown in FIG. 5) was greater than that from the $Si(NEt_2)_2Cl_2$ precursor alone (FIG. 3) Films grown from the precursor mixture (TDEAHf+$Si(NEt_2)_2Cl_2$) showed still higher $SiO_2$ growth rates as shown in FIG. 6. This increased growth rate compared to FIG. 3 is unexpected and should be quite useful for the growth of hafnium silicate films of uniform Hf:Si composition through the thickness of the film.

The films have a mixed Si:Hf composition on the film surface. The constant $SiO_2$ growth rate over the range of 500–600° C. at 2.2 Torr being the same as 0.8 Torr at 600° C. is taken as evidence of mass transport limited deposition over the range of the process. The addition of water vapor or $O_2$, should further decrease the temperature window wherein both Hf and Si alkylamido precursors transport and decompose reliably.

Experiment 2 Prior Art Synthetic Process

When attempts were made to synthesize $Si(NR_2)_4$ R=Et and Me by combining $SiCl_4$ in hexanes with 5 equivalents of $LiNR_2$, only $ClSi(NMe_2)_3$ and $Cl_2Si(NEt_2)_2$ were obtained.

Experiment 3 Synthesis of Tetrakis(Dialkylamino) Silanes $SiCl_4$ reacts with 5 equivalents of $LiNR_2$ initially in a non-polar solvent, such as hexanes. Then the non-polar solvent is pumped off completely under vacuum. Polar solvent is added into the reaction vessel to continue the reaction. The resulting slurry in polar solvent is refluxed for 4–8 hours to facilitate the completion of the reaction.

Experiment 4 Synthesis of Tetrakis (Dimethylamino) Silane

Figure 7:
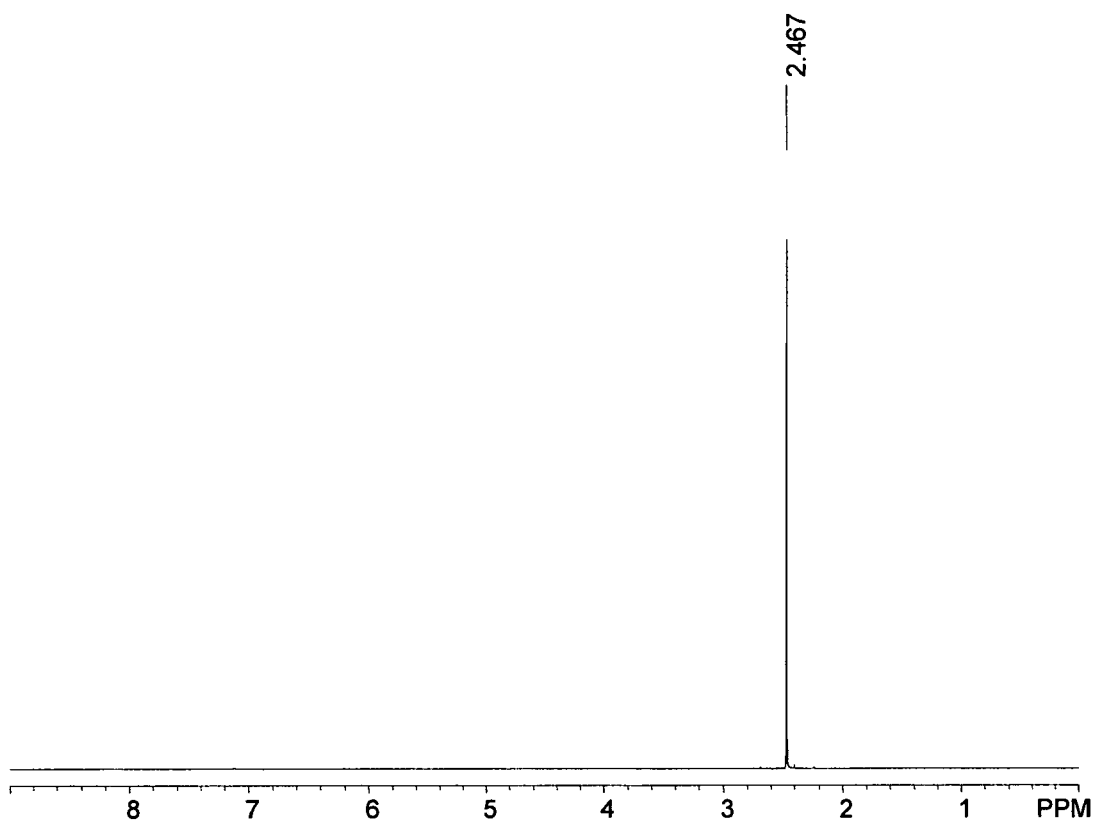
FIG. 7 shows a proton spectrum ($^1$H NMR) of Si(NMe$_2$)$_4$ in (C$_6$D$_6$).

The general reactions were carried out under a steady flow of nitrogen. A 5 L Schlenk flask was charged with 0.8 L of 1.6M solution of n-BuLi in hexane, 1 L of anhydrous hexane and a big magnetic stirring bar. Then 60 g (10% excess) of $HNMe_2$ was bubbled into the Schlenk flask slowly at 0° C., under magnetic stirring. During the addition, very fine white precipitate of $LiNMe_2$ was formed and the reaction mixture became extremely viscous. The mixture was allowed to reach room temperature and then was stirred for an additional 2 h. A solution of $SiCl_4$ (43.5 g, 29.3 mL) in hexane (50 mL) was slowly added to the reaction flask. Moderate heat was generated (exothermic) and the external cooling to 0° C. was applied. Upon completion of $SiCl_4$ addition, the mixture became less viscous. The mixture was allowed to reach room temperature and then was stirred for an additional 2 h. All volatiles were removed in vacuum. Then the reaction flask was charge with 0.5 L of anhydrous THF. The resulting mixture was refluxed for 4 h. THF was removed in vacuum to give a slurry-like mixture of $Si(NMe_2)_4$ and Li salts. 400 mL of hexane were added to extract $Si(NMe_2)_4$ and the resulting mixture was filtered. A second extraction was applied with 100 mL of hexane and a slightly yellow filtrate was obtained. Removal of volatiles under vacuum followed by the vacuum distillation (35° C. at 1 mmHg) gave 31.3 grams of colorless liquid. Yield: 60%. Bp. 35° C. at 1 mmHg. Anal. (calcd., %): C 47.16 (47.06), H 11.42 (11.76), N 26.73 (27.45). Mass spectrum (EI, %): m/z 204 ($M^+$, 70), 160 ($M^+$–$NMe_2$, 100), 116 ($M^+$–2 $NMe_2$, 90). FIG. 7 $^1$H NMR ($C_6D_6$): □2.51 (s, $CH_3$). Residual Cl content is less than 10 ppm (detection limit of analysis).

Experiment 4 Synthesis of Tetrakis (Ethylmethylamino) Silane

A 5 L Schlenk flask was charged with 0.8 L of 1.6M solution of n-BuLi in hexane, 1 L of anhydrous hexane and a big magnetic stirring bar. The reaction mixture was maintained at 0° C. during the addition of HNEtMe (79.3 g, 1.344 mol, 5% excess) solution in hexane (100 mL). Very fine white precipitate of LiNEtMe formed immediately and the reaction mixture became extremely viscous. The mixture was allowed to reach room temperature and then was stirred for an additional hour. A solution of $HSiCl_3$ (43.36 g, 0.32 mol) in hexane (100 mL) was slowly added to the reaction flask. Moderate heat was generated (exothermic) and the external cooling to 0° C. was applied. Upon completion of $HSiCl_3$ addition, the mixture became less viscous. The mixture was allowed to reach room temperature and then was stirred for an additional hour. All volatiles were removed in vacuum. Then the reaction flask was charge with 0.5 L of anhydrous THF. The resulting mixture was refluxed for 4 h. THF was removed in vacuum. 300 mL of hexane were added to extract amidosilanes, the resulting mixture was filtered, and the precipitate was discarded. Removal of volatiles under vacuum followed by the vacuum distillation gave two fractions (28° C. at 0.5 mmHg and 50° C. at 0.3 mmHg) in 4:3 molar rations. The first fraction was confirmed to be $HSi(NEtMe)_3$. The second fraction was identified as $Si(NEtMe)_4$. Yield: 30%. Bp. 50° C. at 0.3 mmHg. Anal. (calcd., %): C 55.61 (55.38), H 12.58 (12.31), N 21.08 (21.54). Mass spectrum (EI, %): m/z 260 ($M^+$, 40), 202 ($M^+$–NEtMe, 70), 144 ($M^+$–2 NEtMe, 50), 86 ($M^+$–3 NEtMe, 100). $^1$H NMR ($C_6D_6$): □2.83 (8H, q, J(H—H)=7 Hz, $CH_2CH_3$), 2.51 (12H, s, $CH_3$), 1.07 (12H, t, J(H—H)=7 Hz, $CH_2CH_3$). $^{13}$C NMR: ($C_6D_6$) □44.68 ($CH_2$–$CH_3$), 35.07 ($CH_3$), 15.01 ($CH_2$–$H_3$).

The features, aspects and advantages of the present invention are further shown with reference to the following non-limiting examples relating to the invention.

The invention claimed is:

1. A method of synthesizing an aminosilane source reagent composition, comprising:
(a) reacting an aminosilane precursor compound with an amine source reagent compound, wherein the amine source reagent compound is selected from the group consisting of:

$B(NR^1R^2)$ and

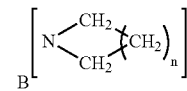

wherein B is selected from the group consisting of H, Li, Na, K, Zn and MgBr; N is nitrogen; $R^1$ and $R^2$ are same or different and each is independently selected from the group consisting of H, aryl, perfluoroaryl, $C_1$–$C_8$ alkyl, and $C_1$–$C_8$ perfluoroalkyl; and n is from 1–6, in a solvent system comprising at least one non-polar solvent, at temperature in a range from about −30° C. to about room temperature, for a period of time sufficient to produce a reaction mixture comprising partially substituted aminosilane components, unreacted aminosilane precursors and unreacted amine components;
  (b) combining the reaction mixture with at least one polar activating solvent component to at least partially solvate and activate the unreacted amine components, wherein the polar activating solvent comprises a Lewis base selected from the group consisting of ethers and tertiary amines; and
  (c) continuing the reaction of step (b) at temperature in a range from about 0° C. to about 100° C. for a period of time sufficient to produce the aminosilane source reagent composition, wherein the aminosilane source reagent composition comprises less than 1000 ppm halogen.

2. The method according to claim 1, wherein the aminosilane precursor compound has reactive leaving groups.

3. The method according to claim 2, wherein the reactive leaving group is selected from the group consisting of H and halogen.

4. The method according to claim 1, wherein the aminosilane precursor compound is selected from the group consisting of silicon halides, alkylsilanes and aminosilanes.

5. The method according to claim 1, wherein the aminosilane precursor compound is a silicon halide compound comprising a composition selected from the group consisting of:

$R^3_xSiA_y(NR^1R^2)_{4-x-y}$ and

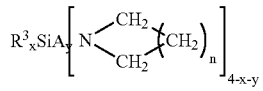

wherein $R^3$ is selected from the group consisting of hydrogen, $C_1$–$C_4$ alkyl, and $C_1$–$C_4$ alkoxy; x is from 0 to 3; Si is silicon; A is halogen; y is from 1 to 4; N is nitrogen; each of $R^1$ and $R^2$ is same or different and is independently selected from the group consisting of H, aryl, perfluoroaryl, $C_1$–$C_8$ alkyl, and $C_1$–$C_8$ perfluoroalkyl; and n is from 1–6.

6. The method according to claim 5, wherein A is Cl.

7. The method according to claim 1, wherein the polar activating solvent is selected from the group consisting of: diethyl ether, tetrahydrofuran (THF), ethylene glycol dimethyl ether (glyme), diethylene glycol dimethyl ether (diglyme), 1,4-dioxane, tetraethylene glycol dimethyl ether (tetraglyme), 1,4,7,10-tetraoxacyclododecane (12-Crown-4), 1,4,7,10,13-pentaoxacyclopentadecane (15-Crown-5), and 1,4,7,10,13,16-hexaoxacyclooctadecane (18-Crown-6), pentamethyldiethylenetriamine (PMDETA), tetramethylethylene-diamine (TMEDA), Triethylamine; (TEA) Diazabicycloun-decene (DBU), Tri-n-butylamine (TNBA), and tetraethylethylenediamine (TEDA).

8. A method of synthesizing an aminosilane source reagent composition, comprising the steps of:
  (1) combining an aminosilane precursor compound comprising at least one halogen leaving group, with an amine source reagent compound, in a solvent system comprising at least one non-polar solvent, for a period of time sufficient to produce a reaction mixture consisting essentially of partially substituted aminosilane components, unreacted aminosilane precursors and unreacted amine components;
  (2) combining with the reaction mixture of step (1) a polar activating solvent to at least partially solvate and activate the unreacted amine components, wherein the polar activating solvent comprises a Lewis base selected from the group consisting of ethers and tertiary amines;
  (3) continuing the reaction of step (2) for a period of time sufficient to provide for essentially stoichiometric substitution of at least one halide on the aminosilane precursor compound by an amine component to produce the aminosilane source reagent composition.

9. The method according to claim 8, wherein the aminosilane source reagent composition comprises less than 1000 ppm halogen.

10. The method according to claim 8, wherein the aminosilane precursor compound has reactive leaving groups.

11. The method according to claim 10, wherein the reactive leaving group is selected from the group consisting of H and halogen.

12. The method according to claim 8, wherein the aminosilane precursor compound is selected from the group consisting of silicon halides, alkylsilanes and aminosilanes.

13. The method according to claim 8, wherein the aminosilane precursor compound is a silicon halide compound comprising a composition selected from the group consisting of:

$R^3_xSiA_y(NR^1R^2)_{4-x-y}$ and

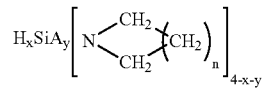

wherein $R^3$ is selected from the group consisting of hydrogen, $C_1$–$C_4$ alkyl, and $C_1$–$C_4$ alkoxy; x is from 0 to 3; Si is silicon; A is halogen; y is from 1 to 4; N is nitrogen; each of $R^1$ and $R^2$ is same or different and is independently selected from the group consisting of H, aryl, perfluoroaryl, $C_1$–$C_8$ alkyl, and $C_1$–$C_8$ perfluoroalkyl; and n is from 1–6.

14. The method according to claim 13, wherein A is Cl.

15. The method according to claim 8, wherein the polar activating solvent is selected from the group consisting of: diethyl ether, tetrahydrofuran (THF), ethylene glycol dimethyl ether (glyme), diethylene glycol dimethyl ether (diglyme), 1,4-dioxane, tetraethylene glycol dimethyl ether (tetraglyme), 1,4,7,10-tetraoxacyclododecane (12-Crown-4), 1,4,7,10,13-pentaoxacyclopentadecane (15-Crown-5), and 1,4,7,10,13,16-hexaoxacyclooctadecane (18-Crown-6), pentamethyldiethylenetriamine (PMDETA), tetramethylethylene-diamine (TMEDA), Triethylamine; (TEA) Diazabicycloun-decene (DBU), Tri-n-butylamine (TNBA), and tetraethylethylenediamine (TEDA).

16. The method according to claim 8, wherein the non-polar solvent is selected from the group consisting of alkanes, alkenes and non-polar aromatics.

17. The method according to claim 8, wherein the amount of the at least one polar activating solvent component is equal to at least one equivalent of the amine source reagent compound.

18. The method according to claim 8, wherein the reaction of steps (2) and (3) is carried out at a temperature that is in the range of from about −30° C. to room temperature.

19. The method according to claim 8, wherein the reaction of steps (2) and (3) is carried out at a temperature that is in the range of from about 0° C. to 100° C.

20. The method according to claim 8, wherein the aminosilane source reagent composition is further purified by distillation.

21. The method according to claim 8, wherein the aminosilane source reagent composition is selected from the group consisting of: $Si(NMe_2)_3Cl$, $Si(NEt_2)_2C_2$, $Si(NMe_2)_4$, $Si(NEt_2)_4$ and $Si(NMeEt)_4$.

22. The aminosilane source reagent composition of claim 21, wherein the aminosilane source reagent composition comprises $Si(NMeEt)_4$.

23. The method according to claim 8, wherein the amine source reagent compound comprises an amine having a composition selected from the group consisting of $B(NR^1R^2)$ and

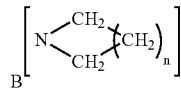

wherein B is selected from the group consisting of H, Li, Na, K, Zn and MgBr; N is nitrogen; $R^1$ and $R^2$ are same or different and each is independently selected from the group consisting of H, aryl, perfluoroaryl, $C_1$–$C_8$ alkyl, and $C_1$–$C_8$ perfluoroalkyl; and n is from 1–6.

24. The method according to claim 23, wherein $R^1$ and $R^2$ are independently selected from the group consisting of methyl and ethyl.

25. A method of synthesizing an aminosilane source reagent composition, comprising the steps of:
   (1) combining an aminosilane precursor compound comprising at least one halogen leaving group, with an amine source reagent compound, in a solvent system comprising at least one non-polar solvent, for a period of time sufficient to produce a reaction mixture consisting essentially of partially substituted aminosilane components, unreacted aminosilane precursors and unreacted amine components;
   (2) removing the non-polar solvent from the reaction mixture;
   (3) combining with the reaction mixture of step (2) a polar activating solvent to at least partially solvate and activate the unreacted amine components;
   (4) continuing the reaction of step (3) for a period of time sufficient to provide for essentially stoichiometric substitution of at least one halide on the aminosilane precursor compound by an amine component to produce the aminosilane source reagent composition.

26. The method according to claim 25, wherein the non-polar solvent is removed by vacuum evaporation.

* * * * *